United States Patent [19]

Martel et al.

[11] Patent Number: 4,521,331
[45] Date of Patent: Jun. 4, 1985

[54] METHOD OF IMPARTING A PLEASANT ODOR

[75] Inventors: Jacques Martel, Bondy; Jean Buendia, Le Perreux-sur-Marne; Francois Nezot, Thiais, all of France

[73] Assignee: Roussel Uclaf, Paris, France

[21] Appl. No.: 438,486

[22] Filed: Nov. 2, 1982

[30] Foreign Application Priority Data

Nov. 10, 1981 [FR] France ................ 81 21009

[51] Int. Cl.$^3$ .................. C11B 9/00; C11D 3/50; A61K 7/16
[52] U.S. Cl. .................. 252/522 R; 252/174.11; 424/49; 424/52; 424/53; 424/65; 424/69; 424/70; 424/76
[58] Field of Search .......... 260/410 R, 464; 252/522 R, 174.11; 560/220, 231; 424/49, 52, 53, 65, 69, 70, 76

[56] References Cited

U.S. PATENT DOCUMENTS

| | | | |
|---|---|---|---|
| 4,258,205 | 3/1981 | Van Berkel et al. | 560/231 |
| 4,298,756 | 11/1981 | Verbrugge et al. | 560/231 |
| 4,298,757 | 11/1981 | Van Berkel et al. | 560/231 |

FOREIGN PATENT DOCUMENTS

| | | | |
|---|---|---|---|
| 43-21057 | 9/1968 | Japan | 560/231 |
| 2025962 | 1/1980 | United Kingdom | 560/231 |
| 2025963 | 1/1980 | United Kingdom | 560/231 |
| 2026483 | 2/1980 | United Kingdom | 560/231 |
| 2108962 | 5/1983 | United Kingdom | 560/231 |

OTHER PUBLICATIONS

Sasaki et al., CA 75:98100d, (1971).
Crombie et al., CA 76:141041v, (1972).
Gaughan et al., CA 91:57187z, (1979).
Bhat et al., CA 95:98036a, (1981).
Sasaki et al., CA 77:62148c, (1972).
Arctander, *Perfume and Flavor Chemicals,* vol. I, Monograph 1187.

*Primary Examiner*—Thomas A. Waltz
*Attorney, Agent, or Firm*—Charles A. Muserlian

[57] ABSTRACT

All possible isomeric forms and mixtures thereof of a compound of the formula

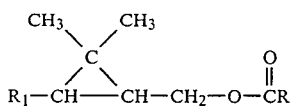

wherein $R_1$ is selected from the group consisting of alkyl of 1 to 8 carbon atoms and alkenyl of 2 to 8 carbon atoms and R is selected from the group consisting of (a) hydrogen, (b) alkyl of 1 to 12 carbon atoms and alkenyl and alkynyl of 2 to 12 carbon atoms optionally substituted with cyano, saturated or unsaturated cycloalkyl or bicycloalkyl of 3 to 12 carbon atoms also optionally substituted, and optionally interrupted by an oxygen atom or containing a keto group, (c) cycloalkyl of 3 to 12 carbon atoms optionally having at least one double bond and at least one alkyl substituent of 1 to 4 carbon atoms, (d) aryl, arylalkyl, aralkenyl and aralkynyl of 6 to 20 carbon atoms optionally substituted on the aryl ring and the alkyl, alkenyl or alkynyl being optionally interrupted with an oxygen or containing a ketone group and (e) heteroaryl, heteroaralkyl, heteroaralkenyl and heteroaralkynyl optionally substituted on the heteroaryl ring and the alkyl, alkenyl and alkynyl being optionally interrupted with an oxygen atom or having a keto group with the proviso that R is not methyl when $R_1$ is 2-methyl-1-propenyl, useful as perfume agents.

7 Claims, No Drawings

METHOD OF IMPARTING A PLEASANT ODOR

STATE OF THE ART

Copending, commonly assigned U.S. patent application Ser. No. 307,629 filed Oct. 1, 1981, now abandoned, Ser. No. 318,445 filed Nov. 5, 1981, now U.S. Pat. No. 4,406,829, Ser. No. 328,994 filed Dec. 9, 1981 and Ser. No. 343,348 filed Jan. 27, 1982, now U.S. Pat. No. 4,431,576, all describe various cyclopropane carboxylic acids esters useful as perfumants. Also pertinent are Gaughan et al [J. Org. Chem., Vol. 44, No. 14 (July, 1979), p. 2441] and Crombie et al [J. Chem. Soc. Perkin Trans I (1972), p. 642–652].

OBJECTS OF THE INVENTION

It is an object of the invention to provide the novel cyclopropane compounds of formula I and a novel process for their preparation.

It is another object of the invention to provide novel odorant compositions and a novel method of imparting a pleasant odor to a composition.

These and other objects and advantages of the invention will become obvious from the following detailed description.

THE INVENTION

The novel compounds of the invention are all possible isomeric forms and mixtures thereof of a compound of the formula

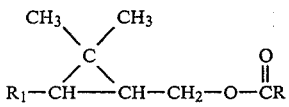

wherein $R_1$ is selected from the group consisting of alkyl of 1 to 8 carbon atoms and alkenyl of 2 to 8 carbon atoms and R is selected from the group consisting of (a) hydrogen, (b) alkyl of 1 to 12 carbon atoms and alkenyl and alkynyl of 2 to 12 carbon atoms optionally substituted with cyano, saturated or unsaturated cycloalkyl or bicycloalkyl of 3 to 12 carbon atoms also optionally substituted, and optionally interrupted by an oxygen atom or containing a keto group, (c) cycloalkyl of 3 to 12 carbon atoms optionally having at least one double bond and at least one alkyl substituent of 1 to 4 carbon atoms, (d) aryl, arylalkyl, aralkenyl and aralkynyl of 6 to 20 carbon atoms optionally substituted on the aryl ring and the alkyl, alkenyl or alkynyl being optionally interrupted with an oxygen or containing a ketone group and (e) heteroaryl, heteroaralkyl, heteroaralkenyl and heteroaralkynyl optionally substituted on the heteroaryl ring and the alkyl, alkenyl and alkynyl being optionally interrupted with an oxygen atom or having a keto group with the proviso that R is not methyl when $R_1$ is 2-methyl-1-propenyl.

The compounds of formula I can exist in numerous possible isomeric forms due to their possession of two asymetric carbon atoms in the 1- and 3-position of the cyclopropane ring and the possibility to have one or more centers or axes of asymetry in the R or $R_1$ portions of the molecule.

Examples of $R_1$ are alkyl such as methyl, ethyl, n-propyl, isopropyl, butyl, iso-butyl, tert.butyl and preferably isopropyl or n-propyl and alkenyl such as 1-propenyl or 2-methyl-1-propenyl.

Examples of R are hydrogen, alkyl such as methyl, ethyl, propyl, isopropyl, butyl, tert.-butyl, isobutyl, n-pentyl, n-hexyl, 2-methyl-pentyl, 2,3-dimethyl-butyl, n-heptyl, 2-methyl-hexyl, 2,2-dimethylpentyl, 3,3-dimethylpentyl, 3-ethyl-pentyl, n-octyl, 2,2-dimethylhexyl, 3,3-dimethyl-hexyl, 3-methyl-3-ethyl-pentyl, nonyl, 2,4-dimethylheptyl and n-decyl; alkyl substituted with optionally unsaturated cycloalkyl such as alkyl substituted with cyclopropyl, cyclobutyl, cyclopentyl, cyclohexyl, cyclopentenyl or cyclohexenyl; alkyl substituted with a substituted cycloalkyl, preferably cycloalkyl substituted alkyl of 1 to 6 carbon atoms such as methyl, —CN, —NO₂ or —COAlkyl of 1 to 6 alkyl carbon atoms such as —COCH₃; alkyl substituted with a bicycloalkyl such as

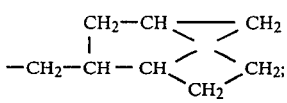

and alkenyl substituted with an unsaturated bicycloalkyl such as

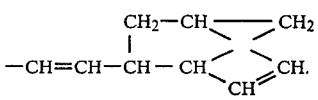

Other Examples of R are alkenyl such as butenyl, isobutenyl or crotonyl; alkynyl such as ethynyl and propynyl; cycloalkyl such as cyclopropyl, cyclobutyl, cyclohexyl, cyclopentyl, cycloheptyl and cyclooctyl; cycloalkyl containing a plurality of double bonds especially 2 double bonds; cycloalkyl substituted with at least one alkyl of 1 to 4 carbon atoms such as methyl, ethyl and n-propyl; optionally aryl, aralkyl, aralkenyl and aralkynyl wherein the aryl is phenyl and the alkyl, alkenyl or alkynyl are as discussed above and the aromatic ring may be substituted in the o-, m- and/or p-positions with at least one member of the group consisting of alkyl of 1 to 4 carbon atoms such as methyl, alkoxy of 1 to 4 carbon atoms such as methoxy, halogen such as chlorine and fluorine, —NO₂, —CF₃, —CN and —COAlk and

and Alk is alkyl of 1 to 12 carbon atoms.

Additional examples of R are optionally substituted heteroaryl such as pyridyl, pyrimidyl, thienyl and furyl; and optionally substituted heteroalkyl, heteroaralkenyl and heteroaralkynyl wherein the alkyl, alkenyl and alkynyl are as discussed above and the substituents are those discussed above for the substituted aryl groups.

Particularly preferred compounds of the invention are those of the formula

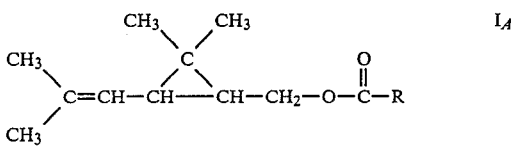

wherein R has the above definitions.

Also may the preferred compounds of formula I are those wherein R is alkyl of 1 to 4 carbon atoms, those wherein R is —(CH$_2$)$_n$—C$_6$H$_5$ and n is 0,1,2,3 or 4, those wherein R is a heteroaryl containing a nitrogen atom and those wherein R is

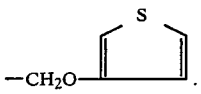

The cyclopropane ring preferably has the 1R,cis or 1R,trans structure.

Specific preferred compounds of the invention are (1R,cis)[2,2-dimethyl-3-(2-methyl-1-propenyl)-cyclopropyl-1-methyl]β-phenyl-propionate, (1R,cis)[2,2-dimethyl-3-(2-methyl-1-propenyl)-cyclopropyl-1-methyl]propionate, (1R,cis)[2,2-dimethyl-3-(2-methyl-1-propenyl)-cyclopropyl-1-methyl]3-thienyloxyacetate and (1R,cis)[2,2-dimethyl-3-(2-methyl-1-propenyl)-cyclopropyl-1-methyl]phenylacetate.

The novel process of the invention for the preparation of the compounds of formula I comprises reacting an alcohol of the formula

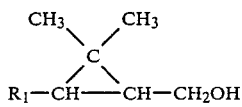

wherein R$_1$ has the above definitions with an acid of the formula

     III wherein R has the above definition or a functional derivative thereof to form the corresponding compound of formula I.

In a preferred mode of the process of the invention, the acid chloride of the acid of formula III is reacted with the alcohol of formula II in the presence of dicyclohexylcarbodiimide but numerous other esterification processes may be used.

The alcohols of formula II are generally known and may be produced by reduction of the corresponding acids or esters.

The novel odorant compositions of the invention are comprised of at least one compound of formula I wherein R$_1$ is defined as above and R is selected from the group consisting of (a) hydrogen, (b) alkyl of 1 to 12 carbon atoms and alkenyl and alkynyl of 2 to 12 carbon atoms optionally substituted with cyano, saturated or unsaturated cycloalkyl or bicycloalkyl of 3 to 12 carbon atoms also optionally substituted, and optionally interrupted by an oxygen atom or containing a keto group, (c) cycloalkyl of 3 to 12 carbon atoms optionally having at least one double bond and at least one alkyl substituent of 1 to 4 carbon atoms, (d) aryl, arylalkyl, aralkenyl, and aralkynyl of 6 to 20 carbon atoms optionally substituted on the aryl ring and the alkyl, alkenyl or alkynyl being optionally interrupted with an oxygen or containing a ketone group and (e) heteroaryl, heteroaralkyl, heteroaralkenyl and heteroaralkynyl optionally substituted on the heteroaryl ring and the alkyl, alkenyl and alkynyl being optionally interrupted with an oxygen atom or having a keto group, in any of their possible isomeric forms and a carrier. The compositions have an agreeable odor such as a floral odor, a flowery odor, a fresh odor, a spice odor or a woody odor.

The preferred compositions have as the active ingredient at least one of (1R,cis)[2,2-dimethyl-3-(2-methyl-1-propenyl)-cyclopropyl-1-methyl]β-phenylpropionate, (1R,cis)[2,2-dimethyl-3-(2-methyl-1-propenyl)-cyclopropyl-1-methyl]propionate, (1R,cis)[2,2-dimethyl-3-(2-methyl-1-propenyl)-cyclopropyl-1-methyl]acetate, (1R,cis)[2,2-dimethyl-3-(2-methyl-1-propenyl)-cyclopropyl-1-methyl]3-thienyloxyacetate and (1R,cis [2,2-dimethyl-3-(2-methyl-1-propenyl)-cyclopropyl-1-methyl]phenylacetate.

The compositions may be used as odorants in perfumes or to prepare odorant compositions which serve as perfume bases. They are also useful in the preparation of hygienic compositions such as soaps, talcum powders, shampoos, dentifrices, bath salts, bath oils or bubble baths, deodorants or in the preparation of cosmetic products such as cremes, makeup milks, lotions, face paint, lipsticks and nail polishes. The compositions may also be used in detergent compositions such as washing powders or the preparation of maintenance products such as waxes or the preparation of insecticides.

The compounds of formula I may be used to impart a pleasant odor to products lacking in odor or to raise up, exalt or modify the odor of compositions having their own odor. They may also be used to mask a disagreeable odor of a product. Naturally, the perfumes, hygienic products, cosmetics, detergent products and maintenance products are prepared by the usual techniques employed in these industries which are largely described in the literature.

The compositions of the invention may contain other usual ingredients such as support vehicles, modifiers, fixing agents, preservatives, stabilizers and other ingredients such as supports, solvents, dispersants and emulsifiers usually used.

When the compounds of formula I are used in perfumes, a small amount of the compounds of formula I is added to other components well known in the perfumery art which may be natural products such as vetiver essence, cedar essence, bergamot orange essence, pine needle essence, lemon essence, jasmin or mandarin orange essence or may be synthetic products such as aldehydes commonly used in perfumery such as hydroxycitronella, ketones such as α-ionone, phenolic compounds such as eugenol, alcohols such as geraniol or lactones such as coumarine.

The amounts of the compounds of formula I used in perfumes will vary greatly as a function of the nature of the specific compound, the use one wishes to make, the intensity of the odor desired as well as, naturally, the nature and composition of the other ingredients added thereto. In perfumes, there may be used 0.1 to 10 parts by weight of the compounds of formula I per 100 parts by weight of the compositions and when used in a perfume base, the base may contain up to 20% by weight of the compound of formula I. When used in detergents, 0.1 to 2 parts by weight of the compounds of formula I per 100 parts by weight of the detergent composition may be used.

The normal method of the invention for imparting a plessant odor to a composition comprises incorporating into a composition an odorantly effective amount of at least one compound of formula I.

In the following examples there are described several preferred embodiments to illustrate the invention. However, it is to be understood that the invention is not intended to be limited to the specific embodiments.

EXAMPLE 1

(1R,cis)[2,2-dimethyl-3-(2-methyl-1-propenyl)-cyclopropyl-1-methyl]trans crotonate 2 ml of pyridine were added at 0° C. to a solution of 3.1 g of (1R,cis)2,2-dimethyl-3-(2-methyl-1-propenyl)-cyclopropyl-methanol, 2.2 g of 2-butenoic acid chloride and 20 ml of benzene and the mixture was stirred at room temperature for 20 hours and poured into a 2N sodium hydroxide solution. The decanted organic phase was dried and evaporated to dryness to obtain 4.4 g of residue. The latter was chromatographed over silica gel and eluted with a 9-1 petroleum ether (b.p. = 40° to 70°)-ether mixture to obtain 1.2 g of (1R,cis)[2,2-dimethyl-3-(2-methyl-1-propenyl)-cyclopropyl-1-methyl]trans crotonate with a specific rotation of $[\alpha]_D^{20} = +38.5° \pm 1.5°$ (c=1% in benzene).

EXAMPLE 2

(1R,cis)[2,2-dimethyl-3-(2-methyl-1-propenyl)-cyclopropyl-1-methyl](R,S)α-methyl-butyrate Using the procedure of Example 1, hexamethylphosphortriamide, 3.1 g of (1R,cis)2,2-dimethyl-3-(2-methyl-1-propenyl)-cyclopropyl-methanol and 2.5 g of 2-methyl-butyric acid chloride were reacted to obtain 4.7 g of product which was chromatographed over silica gel. Elution with a 9-1 petroleum ether (b.p. = 40°-70°)-ether mixture yielded 1.8 g of (1R,cis)[2,2-dimethyl-3-(2-methyl-1-propenyl)-cyclopropyl-1-methyl](R,S)α-methylbutyrate with a specific rotation of $[\alpha]_D^{20} = +14.5° \pm 1°$ (c=1% in benzene).

EXAMPLE 3

(1S,trans)[2,2-dimethyl-3-(2-methyl-1-propenyl)-cyclopropyl-1-methyl[3-methyl-butyrate Using the procedure of Example 1, 3.1 g of (1S,trans)2,2-dimethyl-3-(2-methyl-1-propenyl)-cyclopropylmethanol and 2.5 g of 3-methyl-butyric acid chloride were reacted and the product was chromatographed over silica gel. Elution with a 9-1 petroleum ether (b.p. = 40°-70° C.)-ether mixture yielded 1.6 g of (1S,trans)[2,2-dimethyl-3-(2-methyl-1-propenyl)-cyclopropyl-1-methyl]3-methyl-butyrate with a specific rotation of $[\alpha]_D^{20} = -11.5° \pm 1°$ (c=1% in benzene).

EXAMPLE 4

(1R,trans)[2,2-dimethyl-3-(2-methyl-1-propenyl)-cyclopropyl-1-methyl]3-methyl-butyrate Using the procedure of Example 1, 6.2 g of (1R,trans)2,2-dimethyl-3-(2-methyl-1-propenyl)-cyclopropylmethanol and 4.8 g of 3-methyl-butyric acid chloride in ethyl acetate were reacted and hydrochloric acid was added to the reactor mixture with stirring. The mixture was extracted with ethyl acetate and the organic phase was dried and evaporated to dryness to obtain 4.8 g of (1R,trans)[2,2-dimethyl-3-(2-methyl-1-propenyl)-cyclopropyl-1-methyl]3-methyl-butyrate with a specific rotation of $[\alpha]_D^{20} = +10° \pm 1.5°$ (c=0.85% in benzene).

EXAMPLE 5

(1R,cis)[2,2-dimethyl-3-(2-methyl-1-propenyl)-cyclopropyl-1-methyl]phenylacetate Using the procedure of Example 1, 2 g of (1R,cis)2,2-dimethyl-3-(2-methyl-1-propenyl)-cyclopropane-methanol and 3 ml of phenylacetyl chloride were reacted and the mixture was poured into 2N hydrochloric acid. The mixture was extracted with benene and the extract was washed with water, dried and evaporated to dryness. The residue was chromatographed over silica gel and was eluted with a 95-5 cyclohexane-ethyl acetate mixture to obtain (1R,cis)[2,2-dimethyl-3-(2-methyl-1-propenyl)-cyclopropyl-1-methyl]phenylacetate.

NMR Spectrum (deuterochloroform): Peaks at 0.93 and 1.06 ppm (hydrogens of geminal methyls); at 0.8 and 1.66 ppm (1- and 3-hydrogens of cyclopropane); at 1.72 ppm (hydrogens of methyls of 2-methyl-1-propenyl); at 4–4.13 ppm (hydrogens of —CH$_2$O—); at 3.6 ppm (hydrogen or carbon α to carbonyl of phenylacetyl).

EXAMPLE 6

(1R,cis)[2,2-dimethyl-3-(2-methyl-1-propenyl)-cyclopropyl-1-methyl]β-phenyl-propionate Using the procedure of Example 5, 2 g of (1R,cis)2,2-dimethyl-3-(2-methyl-1-propenyl)-cyclopropane-methanol and 3 ml of β-phenylpropionyl chloride were reacted to obtain 3.2 g of (1R,cis)[2,2-dimethyl-3-(2-methyl-1-propenyl)-cyclopropyl-1-methyl]β-phenyl-propionate NMR Spectrum (deuterochloroform): Peaks at 0.98 and 1.12 ppm (hydrogens of geminal methyls); at 1 to 1.67 ppm (1- and 3-hydrogens of cyclopropyl); at 4.85-4.97 ppm (hydrogens of 1-carbon of 2-methyl-1-propenyl); at 1.68 ppm (hydrogens of methyls of 2-methyl-1-propenyl); at 4.02-4.13 ppm (hydrogens of —CH$_2$O—); at 2.43 to 3.2 ppm (hydrogens of carbons α- and β-to phenylpropionyl); at 7.23 ppm (aromatic hydrogens).

EXAMPLE 7

(1R,cis)[2,2-dimethyl-3-(2-methyl-1-propenyl)-cyclopropyl-1-methyl]propionate

Using the procedure of Example 5, 4 g of (1R,cis)2,2-dimethyl-3-(2-methyl-1-propenyl)-cyclopropane-methanol and 3 ml of propionyl chloride were reacted and the residue was chromatographed over silica gel. Elution yielded 5 g of (1R,cis)[2,2-dimethyl-3-(2-methyl-1-propenyl)-cyclopropyl-1-methyl]propionate.

NMR Spectrum (deuterochloroform): Peaks at 1 and 1.12 ppm (hydrogens of geminal methyls); at 4.83–4.95 ppm (1-hydrogen of 2-methyl-1-propenyl); at 1.68 ppm (hydrogens of methyls of 2-methyl-1-propenyl) at 3.98-4.1 ppm (hydrogens of —CH$_2$—O—); at 1–1.1-1.2 ppm (hydrogens of methyl of propionyl); at 2.12–2.2-.3–2.34–2.45 ppm (hydrogens of carbons α to carbonyl of propionyl).

EXAMPLE 8

(1R,cis)[2,2-dimethyl-3-(2-methyl-1-propenyl)-cyclopropyl-1-methyl]nicotinate

A mixture of 2.4 g of 4-dimethylamino-pyridine and a solution of 2.5 g of nicotinic acid in 200 ml of benzene was stirred for 15 minutes and after 4.5 g of dicyclohexylcarbodiimide were added thereto, the mixture was stirred for 10 minutes. 3.1 g of (1R,cis)2,2-dimethyl-3-(2-methyl-1-propenyl)-cyclopropane-methanol were added to the mixture which was stirred at room temperature for 18 hours and was then filtered. The filtrate was washed with aqueous hydrochloric acid and then with water until the wash waters were neutral. The organic phase was dried and 2 ml of pyridine and 0.8 gm of acetyl chloride were added thereto. The mixture stood at room temperature for 48 hours and the organic phase was washed with aqueous sodium bicarbonate solution to adjust the pH to 9, dried and evaporated to dryness to obtain 5 g of residue. The latter was chromatographed over silica gel and was eluted with a 9-1methylene chloride-ethyl acetate mixture to obtain 1.97 g of (1R,cis)[2,2-dimethyl-3-(2-methyl-1-propenyl)-cyclopropyl-1-methyl]nicotinate with a specific rotation of $[\alpha]_D^{20} = +46° \pm 1.5°$ (c=1% in benzene).

EXAMPLE 9

(1R,cis)2,2-dimethyl-3-(2-methyl-1-propenyl)-cyclopropyl-1-methyl]cyclopentylpropionate Using the procedure of Example 8, 2.85 g of cyclopentypropionic acid and 3.1 g of (1R,cis)2,2-dimethyl-3-(2-methyl-1-propenyl)-cyclopropane-methanol were reacted to obtain 5.5 g of residue. The latter was chromatographed over silica gel and eluted with a 95-5 petroleum ether (b.p.=40°–70° C.)-ether mixture to obtain 3.17 g of (1R,cis)2,2-dimethyl-3-(2-methyl-1-propenyl)-cyclopropyl-1-methyl]cyclopentylpropionate with a specific rotation of $[\alpha]_D^{20} = +31.5° \pm 1°$ (c=1.2% in benzene).

EXAMPLE 10

(1R,cis)[2,2-dimethyl-3-(2-methyl-1-propenyl)-cyclopropyl-1-methyl]3-thienyloxy acetate Using the procedure of Example 8, 3.2 g 3-thienyloxyacetic acid and 3.1 g of (1R,cis)2,2-dimethyl-3-(2-methyl-1-propenyl)-cyclopropane-methanol were reacted to obtain 7 g of residue which was chromatographed over silica gel. Elution with a 9-1cyclohexane-ethyl acetate mixture yielded 2.2 g of (1R,cis)[2,2-dimethyl-3-(2-methyl-1-propenyl)-cyclopropyl-1-methyl]3-thienyloxy-acetate with a specific rotation of $[\alpha]_D^{20} = +29.5° \pm 1.5°$ (c=0.85% in benzene).

EXAMPLES 11 TO 99

Using the procedure of Example 8, the appropriate acid and cyclopropane-methanol were reacted to obtain the compounds in the following Table.

| Example No. | Product | Physical Properties |
|---|---|---|
| 11 | (1R,cis)[2,2-dimethyl-3-(2-methyl-1-propenyl)-cyclopropyl-1-methyl]3-methyl-crotonate | $[\alpha]_D^{20} = +39.5 \pm 1.5°$ (c = 1% in benzene) |
| 12 | (1R,cis)[2,2-dimethyl-3-(2-methyl-1-propenyl)-cyclopropyl-1-methyl]β-ethoxy propionate | $[\alpha]_D^{20} = +38° \pm 1.5°$ (c = 1.2% in benzene) |
| 13 | (1R,cis)[2,2-dimethyl-3-(2-methyl-1-propenyl)-cyclopropyl-1-methyl]4-methyl-valerianate | $[\alpha]_D^{20} = +35.5° \pm 1°$ (c = 1.5% in benzene) |
| 14 | (1R,cis)[2,2-dimethyl-3-(2-methyl-1-propenyl)-cyclopropyl-1-methyl]levulinate | $[\alpha]_D^{20} = +35.5° \pm 1°$ (c = 1.5% in benzene) |
| 15 | (1R,cis)[2,2-dimethyl-3-(2-methyl-1-propenyl)-cyclopropyl-1-methyl]4-acetyl-butyrate | $[\alpha]_D^{20} = +34° \pm 1°$ (c = 1.5% in benzene) |
| 16 | (1S,trans)[2,2-dimethyl-3-(2-methyl-1-propenyl)-cyclopropyl-1-methyl]valerianate | b.p. = 82° C./84° C. under 0.2 mm mercury $[\alpha]_D^{20} = 11.5° \pm 2°$ (c = 0.7% CCl$_4$) |
| 17 | (1R,cis)[2,2-dimethyl-3-(2-methyl-1-propenyl)-cyclopropyl-1-methyl]3,3-dimethyl-butanoate | $[\alpha]_D^{20} = +35° \pm 1°$ (c = 1.5% in benzene) |
| 18 | (1R,cis)[2,2-dimethyl-3-(2-methyl-1-propenyl)-cyclopropyl-1-methyl]phenoxy-acetate | $[\alpha]_D^{20} = +39° \pm 1.5°$ (c = 1.5% in benzene) |
| 19 | (1R,cis)[2,2-dimethyl-3-(2-methyl-1-propenyl)-cyclopropyl-methyl]cyclopentyl-acetate | $[\alpha]_D^{20} = +34° \pm 1.5°$ (c = 1% in benzene) |
| 20 | (1R,cis)[2,2-dimethyl-3-(2-methyl-1-propenyl)-cyclopropyl-1-methyl]octanoate | $[\alpha]_D^{20} = +31.5° \pm 1°$ (c = 1.2% in benzene) |
| 21 | (1R,cis)[2,2-dimethyl-3-(2-methyl-1-propenyl)-cyclopropyl-1-methyl]methoxy-acetate | $[\alpha]_D^{20} = +40° \pm 1°$ (c = 1.5% in benzene) |
| 22 | (1R,cis)[2,2-dimethyl-3-(2-methyl-1-propenyl)-cyclopropyl-1-methyl]2-acetyl-benzoate | $[\alpha]_D^{20} = +33.5° \pm 1.5°$ (c = 0.9% in benzene) |
| 23 | (1R,cis)[2,2-dimethyl-3-(2-methyl-1-propenyl)-cyclopropyl-1-methyl]hexanoate | $[\alpha]_D^{20} = +35° \pm 1.5°$ (c = 1.3% in benzene) |

-continued

| Example No. | Product | Physical Properties |
|---|---|---|
| 24 | (1R,cis)[2,2-dimethyl-3-(2-methyl-1-propenyl)-cyclopropyl]-1-methyl](E) cinnamate | $[\alpha]_D^{20} = +26.5° \pm 1°$ (c = 0.8% in benzene) |
| 25 | (1R,cis)[2,2-dimethyl-3-(2-methyl-1-propenyl)-cyclopropyl-1-methyl]2-cyclopentenylacetate | $[\alpha]_D^{20} +34.5° \pm 1°$ (c = 2% in benzene) |
| 26 | (1R,cis)[2,2-dimenthyl-3-(2-methyl-1-propenyl)-cyclopropyl-1-methyl]cyclohexane carboxylate | $[\alpha]_D^{20} = +38° \pm 2°$ (c = 0.8% in benzene) |
| 27 | (1R,cis)[2,2-dimethyl-3-(2-methyl-1-propenyl)-cyclopropyl-1-methyl]pinonate | $[\alpha]_D^{20} = +28° \pm 2°$ (c = 0.9% in benzene) |

EXAMPLE 28

(1R,cis)[2,2-dimethyl-3-(2-methyl-1ppropenyl-cyclopropyl-1-methyl-cyclopentane carboxylate RMN: $CDCl_3$ ppm.

1 and 1.12H of methyl groups in the 2-position of cyclopropane 4.9–5H of carbon in the 1-position of the 2-methyl-1-propenyl group 0.83 at 2.08H of carbons in the 1 and 3 positions of cyclopropane 1.67H of methyl group of the 2-methyl-1-propenyl group 4–4.13H of $CH_2O$ 2.75H of cyclopentane in a position α to $CO_2$

| Example No. | Product | Physical Properties |
|---|---|---|
| 29 | (1R,cis)[2,2-dimethyl-3-(2-methyl-1-propenyl)-cyclopropyl-1-methyl]2E-furylacrylate | $[\alpha]_D^{20} = +31° \pm 2°$ (c = 0.6% in benzene) |
| 30 | (1R,cis)[2,2-dimethyl-3-(2-methyl-1-propenyl)-cyclopropyl-1-methyl]-cyclobutane carboxylate | $[\alpha]_D^{20} = +40° \pm 2.5°$ C. (c = 0.5% in benzene) |
| 31 | (1R,cis)[2,2-dimethyl-3-(2-methyl-1-propenyl)-cyclopropyl-1-methyl]2(E)-thienylacrylate | $[\alpha]_D^{20} = +26.5° \pm 1°$ (c = 1.8% in benzene) |
| 32 | (1R,cis)[2,2-dimethyl-3-(2-methyl-1-propenyl)-cyclopropyl-1-methyl]2-furoate | $[\alpha]_D^{20} = +39.5° \pm 1.5°$ (c = 1% in benzene) |
| 33 | (1R,cis)[2,2-dimethyl-3-(2-methyl-1-propenyl)-cyclopropyl-1-methyl]-acrylate | $[\alpha]_D^{20} = +47° \pm 1.5°$ (c = 1% in benzene) |
| 34 | (1R,cis)[2,2-dimethyl-3-(2-methyl-1-propenyl)-cyclopropyl-1-methyl]-methacrylate | $[\alpha]_D^{20} = +45.5° \pm 2.5°$ (c = 0.6% in benzene) |
| 35 | (1R,cis)[2,2-dimethyl-3-(2-methyl-1-propenyl)-cyclopropyl-1-methyl]-thienyl carboxylate | $[\alpha]_D^{20} = +40.5° \pm 1.5°$ (c = 1% in benzene) |
| 36 | (1R,cis)[2,2-dimethyl-3-(2-methyl-1-propenyl)-cyclopropyl-1-methyl]-1-methyl-cyclohexane-carboxylate | $[\alpha]_D^{20} = +39.5° \pm 1.5°$ (c = 1.5% in benzene) |
| 37 | (1R,cis)[2,2-dimethyl-3-(2-methyl-1-propenyl)-cyclopropyl-1-methyl]4-pentenoate | $[\alpha]_D^{20} = +38.5° \pm 1.5°$ (c = 1% in benzene) |
| 38 | (1R,cis)[2,2-dimethyl-3-(2-methyl-1-propenyl)-cyclopropyl-1-methyl]-cyclohexylacetate | $[\alpha]_D^{20} = +31.5° \pm 1.5°$ (c = 2% in benzene) |
| 39 | (1R,cis)[2,2-dimethyl-3-(2-methyl-1-propenyl)-cyclopropyl-1-methyl]-3-butenoate | $[\alpha]_D^{20} = +42.5° \pm 1.5°$ (c = 0.9% in benzene) |
| 40 | (1R,cis)[2,2-dimethyl-3-(2-methyl-1-propenyl)-cyclopropyl-1-methyl]-2-ethoxyacetate | $[\alpha]_D^{20} = +37° \pm 1°$ (c = 1.5% in benzene) |
| 41 | (1R,cis)[2,2-dimethyl-3-(2-methyl-1-propenyl)-cyclopropyl-1-methyl]2-methyllevulinate | $[\alpha]_D^{20} = +38.5° \pm 1°$ (c = 1% in benzene) |
| 42 | (1R,cis)[2,2-dimethyl-3-(2- | $[\alpha]_D^{20} = +52° \pm 1.5°$ (c = 1.4% |

-continued

| Example No. | Product | Physical Properties |
|---|---|---|
| | methyl-1-propenyl)-cyclopropyl-1-methyl]-cyanacetate | in benzene) |
| 43 | (1R,cis)[2,2-dimethyl-3-(2-methyl-1-propenyl)-cyclopropyl-1-methyl]-m-cyanobenzoate | $[\alpha]_D^{20} = +29.5° \pm 1°$ (c = 1.5% in benzene) |
| 44 | (1R,cis)[2,2-dimethyl-3-(2-methyl-1-propenyl)-cyclopropyl-1-methyl]-m-cyanophenylacetate | $[\alpha]_D^{20} = +31.5° \pm 1°$ (c = 1.5% in benzene) |
| 45 | (1R,cis)[2,2-dimethyl-3-(2-methyl-1-propenyl)-cyclopropyl-1-methyl]-isonicotinate | $[\alpha]_D^{20} = +43.5° \pm 1°$ (c = 1% in benzene) |
| 46 | (1R,cis)[2,2-dimethyl-3-(2-methyl-1-propenyl)-cyclopropyl-1-methyl]-picolinate | $[\alpha]_D^{20} = +45° \pm 2.5°$ (c = 0.5% in benzene) |
| 47 | (1R,cis)[2,2-dimethyl-3-(2-methyl-1-propenyl)-cyclopropyl-1-methyl]-orthonitrocinnamate | $[\alpha]_D^{20} = +22° \pm 1°$ (c = 1% in benzene) |
| 48 | (1R,cis)[2,2-dimethyl-3-(2-methyl-1-propenyl)-cyclopropyl-1-methyl]4-cyanobenzoate | $[\alpha]_D^{20} = +31° \pm 1°$ (c = 2.2% in benzene) |
| 49 | (1R,cis)[2,2-dimethyl-3-(2-methyl-1-propenyl)-cyclopropyl-1-methyl]-anisate | $[\alpha]_D^{20} = +32° \pm 1°$ (c = 2% in benzene) |
| 50 | (1R,cis)[2,2-dimethyl-3-(2-methyl-1-propenyl)-cyclopropyl-1-methyl]-paramethoxyphenyl-propionate | $[\alpha]_D^{20} = +30.5° \pm 1.5°$ (c = 1.2% in benzene) |
| 51 | (1R,cis)[2,2-dimethyl-3-(2-methyl-1-propenyl-cyclopropyl-1-methyl]-5-norbornene-2-acrylate | $[\alpha]_D^{20} = +27° \pm 1°$ (c = 2% in benzene) |
| 52 | (1R,cis)[2,2-dimethyl-3-(2-methyl-1-propenyl)-cyclopropyl-1-methyl]-ortho-methoxy phenyl-propionate | $[\alpha]_D^{20} = +30° \pm 1°$ (c = 1.5% in benzene) |
| 53 | (1R,cis)[2,2-dimethyl-3-(2-methyl-1-propenyl)-cyclopropyl-1-methyl]-ortho-methoxy-cinnamate | $[\alpha]_D^{20} = +22.5° \pm 1°$ (c = 0.8% in benzene) |
| 54 | (1R,cis)[2,2-dimethyl-3-(2-methyl-1-propenyl)-cyclopropyl-1-methyl]-meta-nitro-cinnamate | $[\alpha]_D^{20} = +21.5° \pm 2°$ (c = 0.8% in benzene) |
| 55 | (1R,cis)[2,2-dimethyl-3-(2-methyl-1-propenyl)-cyclopropyl-1-methyl]-2-pyrrole carboxylate | $[\alpha]_D^{20} = +38° \pm 2°$ (c = 0.5% in benzene) |
| 56 | (1R,cis)[2,2-dimethyl-3-(2-methyl-1-propenyl)-cyclopropyl-1-methyl]4-(2-thienyl)-butyrate | $[\alpha]_D^{20} = +27° \pm 1°$ (c = 1.5% in benzene) |
| 57 | (1R,cis)[2,2-dimethyl-3-(2-methyl-1-propenyl)-cyclopropyl-1-methyl]-ortho-cyanobenzoate | $[\alpha]_D^{20} = +54.5° \pm 2.5°$ (c = 0.5% in benzene) |
| 58 | (1R,cis)[2,2-dimethyl-3-(2-methyl-1-propenyl)-cyclopropyl-1-methyl]-citronellate | $[\alpha]_D^{20} = +30° \pm 2°$ (c = 0.8% in benzene) |
| 59 | (1R,cis)[2,2-dimethyl-3-(2-methyl-1-propenyl)-cyclopropyl-1-methyl]-(2-methoxyphenoxy)-acetate | $[\alpha]_D^{20} = +31° \pm 3°$ (c = 0.3% in benzene) |
| 60 | (1R,cis)[2,2-dimethyl-3-(2-methyl-1-propenyl)-cyclopropyl-1-methyl]4-(methylthio)-benzoate | $[\alpha]_D^{20} = +26.5° \pm 3°$ (c = 0.3% in benzene) |
| 61 | (1R,cis)[2,2-dimethyl-3-(2-methyl-1-propenyl)-cyclopropyl-1-methyl]2-norbornane-acetate | $[\alpha]_D^{20} = +29° \pm 2.5°$ (c = 0.5% in benzene) |
| 62 | (1R,cis)[2,2-dimethyl-3-(2-methyl-1-propenyl)-cyclopropyl-1-methyl](RS) 3-methyl-valerate | $[\alpha]_D^{20} = +35° \pm 1°$ (c = 1% in benzene) |
| 63 | (1R,cis)[2,2-dimethyl-3(2-methyl-1-propenyl)-cyclo- | $[\alpha]_D^{20} = +37.5° \pm 0.5°$ (c = 2% in benzene) |

-continued

| Example No. | Product | Physical Properties |
|---|---|---|
| 64 | propyl-1-methyl]3-furoate (1S,cis)[2,2-dimethyl-3-(2-methyl-1-propenyl)-cyclopropyl-1-methyl]heptanoate | $[\alpha]_D^{20} = -39° \pm 2°$ (c =0.7% in benzene) |
| 65 | (1S,cis)[2,2-dimethyl-3-(2-methyl-1-propenyl)-cyclopropyl-1-methyl]pivalate | $[\alpha]_D^{20} = -67° \pm 1°$ (c = 1.9% in benzene) |
| 66 | (1R,trans)[2,2-dimethyl-3-(2-methyl-1-propenyl-cyclopropyl-1-methyl]pivalate | $[\alpha]_D^{20} = +25° \pm 1°$ (c = 0.9% in ethanol) |

EXAMPLE 67

(1R,cis)[2,2-dimethyl-3-(2-methyl-1-propyl)-cyclopropyl-1-methyl]pellargonate

RMN: CDCl$_3$ ppm.

1 at 1.12H of methyl groups in the 2-position of cyclopropane
4.8H of methyl groups of the 2-methyl-1-propenyl group
4.8–4.9H of carbon in the 1-position of the 2-methyl-1-propenyl groups
3.97–4.1H of CH$_2$O
2.17–2.28–2.39H of the carbon of the heptanoyl group in a position α to CO$_2$
0.88H of end methyl of the heptanoy group.

1.28 Other H of the heptanoy group

EXAMPLE 68

(1R,cis)[2,2-dimethyl-3-(2-methyl-1-propenyl)-cyclopropyl-1-methyl]n-butyrate 1 at 1.12H of methyl group in the 2-position of cyclopropane
4.83–4.95H of methyl groups of the 2-methyl-1-propenyl group
1.68H of carbon in the 1-position of the 2-methyl-1-propenyl groups
3.98–4.1H of CH$_2$O
2.15–2.38H of the butyryl groups in a position α to CO$_2$
0.83–0.95–1.05H of methyl group of the butyryl group.

| Example No. | Product | Physical Properties |
|---|---|---|
| 69 | (1S,cis)[2,2-dimethyl-3-(2-methyl-1-propenyl)-cyclopropyl-1-methyl](RS)2-methyl-butyrate | $[\alpha]_D^{20} = -48° \pm 1.5°$ (c = 1.5% in benzene) |
| 70 | (1R,cis)[2,2-dimethyl-3-(2-methyl-1-propenyl)-cyclopropyl-1-methyl]-2-methoxy-carbonyl-acetate | $[\alpha]_D^{20} = +41° \pm 1.5°$ (c = 1% in benzene) |
| 71 | (1R,cis)[2,2-dimethyl-3-(2-methyl-1-propenyl)-cyclopropyl-1-methyl]2(RS) ethyl-hexanoate | $[\alpha]_D^{20} = +37° \pm 2°$ (c = 0.6% in benzene) |
| 72 | (1R,cis)[2,2-dimethyl-3-(2-methyl-1-propenyl)-cyclopropyl-1-methyl]-cyclopropane carboxylate | $[\alpha]_D^{20} = +33.5° \pm 2°$ (c = 0.6% in benzene) |
| 73 | (1R,cis)[2,2-dimethyl-3-(2-methyl-1-propenyl)-cyclopropyl-1-methyl]isovalerate | $[\alpha]_D^{20} = +41° \pm 1°$ (c = 1.7% in benzene) |
| 74 | (1R,cis)[2,2-dimethyl-3-(2-methyl-1-propenyl)-cyclopropyl-1-methyl]pivalate | $[\alpha]_D^{20} = +49.5° \pm 1°$ (c = 2% in benzene) |
| 75 | (1R,cis)[2,2-dimethyl-3-(2-methyl-1-propenyl)-cyclopropyl-1-methyl]heptanoate | $[\alpha]_D^{20} = +34° \pm 1°$ (c =0.95% in benzene) |
| 76 | (1S,trans)[2,2-dimethyl-3-(2-methyl-1-propenyl)-cyclopropyl-1-methyl](RS)α-methyl-butyrate | $[\alpha]_D^{20} = -15° \pm 1°$ (c = 0.9% in benzene) |
| 77 | (1S,trans)[2,2-dimethyl-3-(2-methyl-1-propenyl)-cyclopropyl-1-methyl]pivalate | $[\alpha]_D^{20} = -19° \pm 1°$ (c = 1% in benzene) |
| 78 | (1S,trans)[2,2-dimethyl-3-(2-methyl-1-propenyl)-cyclopropyl-1-methyl]-heptanoate | $[\alpha]_D^{20} = -9° \pm 1°$ (c = 1% in benzene) |
| 79 | (1R,trans)[2,2-dimethyl-3-(2-methyl-1-propenyl)-cyclopropyl-1-methyl]heptanoate | $[\alpha]_D^{20} = +16° \pm 1°$ (c = 1% in ethanol) |
| 80 | (1R,cis)[2,2-dimethyl-3-(2-methyl-1-propenyl)-cyclopropyl-1-methyl]benzoate | b.p. = 105° C. ± 5° (0.1 mm mercury) $[\alpha]_D^{20} = +45° \pm 1.5°$ (c = 1% in CCl$_4$) |
| 81 | (1R,cis)[2,2-dimethyl-3-(2- | $[\alpha]_D^{20} = +59.5° \pm 1°$ (c = 2% |

-continued

| Example No. | Product | Physical Properties |
|---|---|---|
| | methyl-1-propenyl)-cyclopropyl-1-methyl]formiate | in benzene) |
| 82 | (1R,trans)[2,2-dimethyl-3-(2-methyl-1-propenyl)-cyclopropyl-1-methyl](RS)2-methyl-butyrate | $[\alpha]_D^{20} = +22° \pm 1.5°$ (c = 0.75% EtOH) |
| 83 | (1R,trans)[2,2-dimethyl-3-(2-methyl-1-propenyl)-cyclopropyl-1-methyl]valerianate | $[\alpha]_D^{20} = +13° \pm 1.5°$ (c = 0.7% in CCl$_4$) |
| 84 | (1R,cis)[2,2-dimethyl-3-(2-methyl-1-propenyl)-cyclopropyl-1-methyl]valerianate | $[\alpha]_D^{20} = +46° \pm 1°$ (c = 1.2% in CCl$_4$) |
| 85 | (1S,cis)[2,2-dimethyl-3-(2-methyl-1-propenyl)-cyclopropyl-1-methyl]valerianate | $[\alpha]_D^{20} = -46.5° \pm 1.5°$ (c = 1% CCl$_4$) |
| 86 | (1S,cis)[2,2-dimethyl-3-(2-methyl-1-propenyl)-cyclopropyl-l-methyl]benzoate | $[\alpha]_D^{20} = -46° \pm 2°$ (c = 1% CCl$_4$) |
| 87 | (1R,trans)[2,2-dimethyl-3-(2-methyl-1-propenyl)-cyclopropyl-1-methyl]-benzoate | $[\alpha]_D^{20} = +3.5° \pm 3°$ (c = 0.5% CCl$_4$) |
| 88 | (1S,trans)[2,2-dimethyl-3-(2-methyl-1-propenyl)-cyclopropyl-1-methyl]-benzoate | $[\alpha]_D^{20} = 0° \pm 3°$ (CCl$_4$) |
| 89 | (1RS,cis,trans)[2,2-dimethyl-3-(2-methyl-1-propenyl)-cyclopropyl-1-methyl]-5-benzyl-furoate | $n_D = 1.529$ |
| 90 | (1R,trans)[2,2-dimethyl-3-(2-methylpropyl)-cyclopropyl-1-methyl]-3-methylbutyrate | $[\alpha]_D^{20} = +8° \pm 2°$ (c = 0.65% ethanol) |
| 91 | (1R,cis)[2,2-dimethyl-3-(2-methylpropyl)-cyclopropyl-1 methyl]-pivalate | Analysis: C$_{15}$H$_{28}$O$_2$ molecular weight = (240.37) Calculated: % C 74.94  % H 11.74 Found: % C 74.6  % H 11.8 |
| 92 | (1R,cis)[2,2-dimethyl-3-(2-methylpropyl)-cyclopropyl-1-methyl]-heptanoate | Analysis: C$_{17}$H$_{32}$O$_2$ molecular weight = (268.35) Calculated: % C 76.06  % H 12.02 Found: % C 76.0  % H 12.4 |
| 93 | (1S,cis)[2,2-dimethyl-3-(2-methylpropyl)-cyclopropyl-1-methyl]-crotonate | $[\alpha]_D^{20} = +4° \pm 1°$ (c = 1.5% in benzene) |
| 94 | (1R,trans)[2,2-dimethyl-3-(cyclobutylidene-methyl]-cyclopropyl-l-methyl]isobutyrate | $[\alpha]_D^{20} = -5° \pm 1°$ (c = 1.3% in CHCl$_3$) |
| 95 | (1R,trans)[2,2-dimethyl-3-(cyclobutylidene-methyl]-cyclopropyl-1-methyl]propionate | $[\alpha]_D^{20} = -8° \pm 1°$ (c = 1.5% in CHCl$_3$) |
| 96 | (1R,trans)[2,2-dimethyl-3-(2-methyl-1-propenyl)-cyclopropyl-1-methyl]propionate | b.p.$_{0.5}$ = 65° C. |
| 97 | (1R,trans)[2,2-dimethyl-3-(2-methyl-1-propenyl)-cyclopropyl-1-methyl]3-phenyl-propionate | Analysis: C$_{19}$H$_{26}$O$_2$ molecular weight: (286.417) Calculated: % C 79.68  % H 9.15 Found: % C 79.4  % H 9.1 |
| 98 | (1S,trans)[2,2-dimethyl-3-(2-methyl-1-propenyl)-cyclopropyl-1-methyl]3-phenyl-propionate | IR specta (CHCl$_3$) Absorption at 1722 cm$^{-1}$ (c = 0 ester) 1600 and 1492 cm$^{-1}$ (aromatic bands) 1380 cm$^{-1}$ (gem. di Me) 645 cm$^{-1}$ (aromatic deformation) |
| 99 | (1S,cis)[2,2-dimethyl-3-(2-methyl-1-propenhy)-cyclopropyl-1-methyl]3-phenyl-propionate | IR spectra (CHCl$_3$) Absorption at 1722 cm$^{-1}$ (c = 0 ester) 1380 cm$^{-1}$ (gem. di Me) 1600 and 1492 cm$^{-1}$ (aromatic bands) 645 cm$^{-1}$ (aromatic deform- |

EXAMPLE 100

(1R,cis)[2,2-dimethyl-3-(1Z-propenyl)-cyclopropyl-1-methyl]formate

A mixture of 2.8 of (1R,cis)2,2-dimethyl-3-(1Z-propenyl)-cyclopropane-methanol, 1.8 ml of formic acid, 12.8 ml of triethylamine, 2 g of 4-dimethylaminopyridine and 110 ml of methylene chloride was cooled to −40° C. and 3 g of acetic anhydride were added thereto. The mixture was held at −35° C. for 30 minutes and the temperature was allowed to rise to 20° C. The mixture was stirred at 20° C. for one hour, was washed with 2N hydrochloric acid, with aqueous saturated sodium bicarbonate solution, was dried and evaporated to dryness. The residue was chromatographed over silica gel and was eluted with a 95-5 cyclohexane-ethyl acetate mixture to obtain 1.28 g of (1R,cis)[2,2-dimethyl-3-(1Z-propenyl)-cyclopropyl-1-methyl]formate with a specific rotation of $[\alpha]_D^{20} = +63.5° \pm 1.5°$ (c=1% in benzene).

EXAMPLES 101 to 113

Using the procedure of Example 100, the appropriate acid and cyclopropane-methanol were reacted to form the compounds in the following

TABLE

| Example No. | Product | Physical Properties |
|---|---|---|
| 101 | By operating analogously to that described in Example 100, but starting from 3.1 g of the corresponding alcohol, 1.74 g of (1R,cis)[2,2-dimethyl-3-(1Z-butenyl)-cyclopropyl-1-methyl]formate was obtained | $[\alpha]_D^{20} = +58.5° \pm 1.5°$ (c = 1.7% in benzene) |
| 102 | By operating analogously to that described in Example 100, but starting from 2.4 g of the corresponding alcohol. 1.04 g of (1R,cis)[2,2-dimethyl-3-ethenyl-cyclopropyl-1-methyl]formate was obtained | $[\alpha]_D^{20} = +57.5° \pm 1.5°$ (c = 1% in benzene) |

While operating as described in Example 1, the following products were prepared

| Example No. | Product | Physical Properties |
|---|---|---|
| 103 | (1R,cis) [2,2-dimethyl-3-propyl-cyclopropyl-1-methyl]acetate | $[\alpha]_D^{20} = -15° \pm 1°$ (c = 1% in benzene) |
| 104 | (1S,cis)[2,2-dimethyl-3-(2-methyl-propyl)-cyclopropyl-1-methyl]acetate | $[\alpha]_D^{20} = +8.5° \pm 1°$ (c = 1.3% in benzene) |
| 105 | (1S,trans)[2,2-dimethyl-3-(2-methylpropyl)-cyclopropyl-1-methyl]acetate | $[\alpha]_D^{20} = +3° \pm 1°$ (c = 1% in benzene) |
| 106 | (1R,cis)[2,2-dimethyl-3-(2-methylpropyl)-cyclopropyl-1-methyl]acetate | Analysis: $C_{12}H_{22}O_2$ molecular weight = (198.30) Calculated: % C 72.67  % H 11.18 Found: % C 72.4  % H 11.2 |
| 107 | (1R,trans)[2,2-dimethyl-3-(2-methylpropyl-cyclopropyl-1-methyl]acetate | $[\alpha]_D^{20} = -4° \pm 2°$ (c = 0.4% in benzene) |
| 108 | (1R,cis)[2,2-dimethyl-3-(1Z-butenyl)-cyclopropyl-1-methyl]acetate | $[\alpha]_D^{20} = +45.5° \pm 2.5°$ (c = 0.5% in benzene) |
| 109 | (1R,cis)[2,2-dimethy-3-(1Z-propenyl)-cyclopropyl-1-methyl]acetate | $[\alpha]_D^{20} = +48° \pm 1.5°$ (c = 1% in benzene) |
| 110 | (1R,cis)[2,2-dimethyl-3-ethenyl-cyclopropyl-1-methyl]acetate | $[\alpha]_D^{20} = +44.5° \pm 1.5°$ (c = 1% in benzene) |
| 111 | (1R,trans)[2,2-dimethyl-3-(cyclobutylene-methyl)-cyclopropyl-1-methyl]acetate | $[\alpha]_D^{20} = -8° \pm 1°$ (c = 1.2% in benzene) |
| 112 | (1R,cis)[2,2-dimethyl-3-(cyclobutylidene-methyl)-cyclopropyl-1-methyl]-acetate | $[\alpha]_D^{20} = +70°$ (c = 0.7% in CHCl₃) $n_D^{12} = 1.4878$. |
| 113 | (1R,trans)[2,2-dimethyl-3-(4-methyl-penta-1,3-dienyl)-cyclopropyl-1-methyl]acetate | $[\alpha]_D^{20} = +19°$ (c = 1.2% in CHCl₃) $n_D^{23} = 1.4992$ |

EXAMPLE 114

| Product of Example | Odor given off |
|---|---|
| 2 | wooded celluloid, strawberry, clove |
| 4 | marine algae |
| 6 | chocolate, cistus base |
| 7 | pungent, parsley, linalol, herbaceous, anise |
| 11 | fruity, lavender, geranie-fresh |

EXAMPLE 115

A "rose" composition was prepared containing the following ingredients (parts by weight): 100 parts of the product of Example 4, 15 parts of Ionone, 15 parts of Aldehyde C 9 I/10 PDG, 15 parts of musk ketone, 30 parts of Benjoin resinoid, 40 parts of citronella acetate, 60 parts of bourbon Rhodine, 170 parts of phenethanol, 15 parts of methylionone, 15 parts of Nerol, 45 parts of geranylacetate, 300 parts of citronellol and 180 parts of terpene-free geranium.

EXAMPLE 116

An "Opoponaz" composition was prepared containing 100 parts of the product of Example 6, 65 parts of Musk seed, 40 parts of musk ketone, 25 parts of Benjoin resinoid, 40 parts of vanillin, 75 parts of gamma methylionone, 80 parts of coumarine, 40 parts of Castoreum resinoid, 125 parts of Sandalol, 60 parts of vetyverol, 10 parts of rose essence, 10 parts of iron-free Patchouli, 20 parts of Fch Neroli 131 and 310 parts of orange Bergamot.

EXAMPLE 117

A toilet soap was prepared containing 5 parts by weight of the product of Example 6 and 1000 parts by weight of a commercial soap paste. A commercial powdered detergent was also prepared containing 1 part of the product of Example 7 per 1000 parts of the detergents.

Various modifications of the products and process of the invention may be made without departing from the spirit or scope thereof and it is to be understood that the invention is intended to be limited only as defined in the appended claims.

What we claim is:

1. A perfume containing an odorantly effective amount of at least one compound of the formula

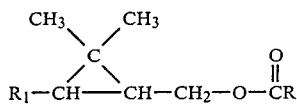

wherein $R_1$ is selected from the group consisting of alkyl of 1 to 8 carbon atoms and alkenyl of 2 to 8 carbon atoms and R is selected from the group consisting of (a) hydrogen, (b) alkyl of 1 to 12 carbon atoms and alkenyl and alkynyl of 2 to 12 carbon atoms optionally substituted with cyano, saturated or unsaturated cycloalkyl or bicycloalkyl of 3 to 12 carbon atoms also optionally substituted with at least one alkyl of 1 to 4 carbon atoms, —CN, —NO$_2$ or —COAlkyl of 1 to 6 carbon atoms, and optionally interrupted by an oxygen atom or containing a keto group, (c) cycloalkyl of 3 to 12 carbon atoms optionally having at least one double bond and at least one alkyl substituent of 1 to 4 carbon atoms, (d) aryl, arylalkyl, aralkenyl and aralkynyl of 6 to 20 carbon atoms optionally substituted on the aryl ring with at least one member of the group consisting of alkyl of 1 to 4 carbon atoms, alkoxy of 1 to 4 carbon atoms, halogen, —NO$_2$, —CF$_3$, —CN and —COAlk and

and Alk is alkyl of 1 to 12 carbon atoms and the alkyl, alkenyl or alkynyl being optionally interrupted with an oxygen or containing a ketone group and (e) heteroaryl, heteroaralkyl, heteroaralkenyl and heteroaralkynyl optionally substituted on the aryl ring with at least one member of the group consisting of alkyl of 1 to 4 carbon atoms, alkoxy of 1 to 4 carbon atoms, halogen, —NO$_2$, —CF$_3$, —CN and —COAlk and

and Alk is alkyl of 1 to 12 carbon atoms and the alkyl, alkenyl and alkynyl being optionally interrupted with an oxygen atom or having a keto group and customary perfumery ingredients.

2. A method of imparting a pleasant odor to a composition comprising adding to the composition a sufficient amount of at least one compound of the formula

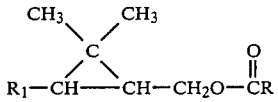

wherein $R_1$ is selected from the group consisting of alkyl of 1 to 8 carbon atoms and alkenyl of 2 to 8 carbon atoms and R is selected from the group consisting of (a) hydrogen, (b) alkyl of 1 to 12 carbon atoms and alkenyl and alkynyl of 2 to 12 carbon atoms optionally substituted with cyano, saturated or unsaturated cycloalkyl or bicycloalkyl of 3 to 12 carbon atoms also optionally substituted with at least one alkyl of 1 to 4 carbon atoms, —CN, —NO$_2$ or —COAlkyl of 1 to 6 alkyl carbon atoms, and optionally interrupted by an oxygen atom or containing a keto group, (c) cycloalkyl of 3 to 12 carbon atoms optionally having at least one double bond and at least one alkyl substituent of 1 to 4 carbon atoms, (d) aryl, arylalkyl, aralkenyl and aralkynyl of 6 to 20 carbon atoms optionally substituted on the aryl ring with at least one member of the group consisting of alkyl of 1 to 4 carbon atoms, alkoxy of 1 to 4 carbon atoms halogen, —NO$_2$, —CF$_3$, —CN and —COAlk and

and Alk is alkyl of 1 to 12 carbon atoms and the alkyl, alkenyl and alkynyl being optionally interrupted with an oxygen or containing a ketone group and (e) heteroaryl, heteroaralkyl, heteroaralkenyl and heteroaralkynyl optionally substituted on the aryl ring with at least one member of the group consisting of alkyl of 1 to 4 carbon atoms, alkoxy of 1 to 4 carbon atoms, halogen, —NO$_2$, —CF$_3$, —CN and —COAlk and

and Alk is alkyl of 1 to 12 carbon atoms and the alkyl, alkenyl and alkynyl being optionally interrupted with an oxygen atom or having a keto group, to impart a pleasant odor.

3. A method of claim 2 wherein the active compound has the formula

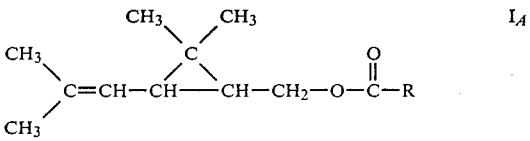

wherein R has the definitions given in claim 2.

4. A method of claim 2 wherein the active compound has R selected from the group consisting of alkyl of 1 to 4 carbon atoms, —(CH$_2$)$_n$—φ, heteroaryl containing a nitrogen atom and

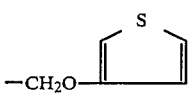

and n is 0, 1, 2, 3 or 4.

5. A method of claim 2 wherein the cyclopropane ring has a 1R,cis or 1R,trans structure.

6. A method of claim 2 wherein the active compound is selected from the group consisting of (1R,cis)[2,2-dimethyl-3-(2-methyl-1-propenyl)-cyclopropyl-1-methyl]β-phenyl-propionate, (1R,cis)[2,2-dimethyl-3-(2-methyl-1-propenyl)-cyclopropyl-1-methyl]propionate, (1R,cis)[2,2-dimethyl-3-(2-methyl-1-propenyl)-cyclopropyl-1-methyl]3-thienyloxyacetate and (1R,cis)[2,2-dimethyl-3-(2-methyl-1-propenyl)-cyclopropyl-1-methyl]phenylacetate.

7. A method of claim 2 wherein the compound is selected from the group consisting of (1R,cis)[2,2-dimethyl-3-(2-methyl-1-propenyl)-cyclopropyl-1-methyl](R,S)2-methyl-butyrate, (1R,trans)[2,2-dimethyl-3-(2-methyl-1-propenyl)-cyclopropyl-1-methyl]3-methyl-butyrate and (1R,cis)[2,2-dimethyl-3-(2-methyl-1-propenyl)-cyclopropyl-1-methyl]3-methyl-crotonate.

* * * * *

UNITED STATES PATENT AND TRADEMARK OFFICE
CERTIFICATE OF CORRECTION

PATENT NO. : 4,521,331

DATED : June 4, 1985

Page 1 of 2

INVENTOR(S) : JACQUES MARTEL, JEAN BUENDIA and FRANCOIS NEZOT

It is certified that error appears in the above-identified patent and that said Letters Patent are hereby corrected as shown below:

| Col. | Line | Example | | |
|---|---|---|---|---|
| 10 | 3rd Col. | 29 | "$-31° = 2°$" should be | — $+31° \pm 2°$— |
| | | 30 | "$-40° = 2.5°$" should be | — $+40° \pm 2.5°$— |
| | | 31 | "$-26.5° = 1°$" should be | — $+26.5° \pm 1°$— |
| | | 32 | "$-39.5° = 1.5°$" should be | — $+39.5° \pm 1.5°$— |
| | | 33 | "$-47° = 1.5°$" should be | — $+47° \pm 1.5°$— |
| | | 34 | "$-45.5° = 2.5°$" should be | — $+45.5° \pm 2.5°$— |
| | | 35 | "$-40.5° = 1.5°$" should be | — $+40.5° \pm 1.5°$— |
| | | 36. | "$-39.5° = 1.5°$" should be | — $+39.5 \pm 1.5°$— |
| | | 37 | "$-38.5° = 1.5°$" should be | — $+38.5° \pm 1.5°$— |
| | | 38 | "$-31.5° = 1.5°$" should be | — $+31.5° \pm 1.5°$— |
| | | 39 | "$-42.5° = 1.5°$" should be | — $+42.5° \pm 1.5°$— |
| | | 40 | "$-37° = 1°$" should be | — $+37° \pm 1°$— |
| | | 41 | "$-38.5° = 1°$" should be | — $+38.5° \pm 1°$— |
| | | 42 | "$-52° = 1.5°$" should be | — $+52° \pm 1.5°$— |

UNITED STATES PATENT AND TRADEMARK OFFICE
CERTIFICATE OF CORRECTION

PATENT NO. : 4,521,331  
DATED : June 4, 1985  
INVENTOR(S) : JACQUES MARTEL, JEAN BUENDIA and FRANCOIS NEZOT Page 2 of 2

It is certified that error appears in the above-identified patent and that said Letters Patent are hereby corrected as shown below:

| Col. | Line | Example | |
|---|---|---|---|
| 18 | 3rd Col. | 108 | "-45.5° = 2.5°" should be -- +45.5° ± 2.5°-- |
| | | 109 | "-48° = 1.5°" should be -- +48° ± 1.5°-- |
| | | 110 | "-44.5° = 1.5°" should be --+44.5° ± 1.5°-- |
| | | 111 | "-8° = 1°" should be -- +8° ± 1°-- |
| | | 112 | "-70°" should be --+70°-- |
| | | 113 | "-19°" should be --+19°-- |

Signed and Sealed this

Seventh Day of January 1986

[SEAL]

Attest:

DONALD J. QUIGG

*Attesting Officer*  *Commissioner of Patents and Trademarks*